United States Patent [19]
Maurice et al.

[11] Patent Number: 4,564,016
[45] Date of Patent: Jan. 14, 1986

[54] APPARATUS FOR INTRODUCING IONIZED DRUGS INTO THE POSTERIOR SEGMENT OF THE EYE AND METHOD

[75] Inventors: David M. Maurice, Atherton, Calif.; Darrell Brooks, Lathrop, Mo.

[73] Assignee: The Board of Trustees of the Leland Stanford Junior University, Palo Alto, Calif.

[21] Appl. No.: 639,806

[22] Filed: Aug. 13, 1984

Related U.S. Application Data

[63] Continuation of Ser. No. 381,151, May 24, 1982, abandoned.

[51] Int. Cl.$^4$ .............................................. A61B 10/00
[52] U.S. Cl. ..................................... 128/645; 604/20; 604/289
[58] Field of Search ...................... 128/76.5, 305, 645, 128/646, 745; 604/20, 21, 27, 28, 35-37, 289, 290, 294, 295, 297, 301, 313, 316, 334

[56] References Cited

U.S. PATENT DOCUMENTS

| 603,815 | 5/1898 | Duke | 604/289 |
| 2,525,381 | 10/1950 | Tower | 604/20 |
| 3,207,150 | 9/1965 | Uddenberg | 604/289 |
| 3,664,340 | 5/1972 | Morgan | 604/295 |
| 4,111,200 | 9/1978 | Sbarra et al. | 604/301 |
| 4,340,047 | 7/1982 | Tapper et al. | 604/20 |

OTHER PUBLICATIONS

"Corneal Surgery", vol. 2, The C. V. Mosby Corporation, 1981, by Girard.

Primary Examiner—Edward M. Coven
Assistant Examiner—Max F. Hindenburg
Attorney, Agent, or Firm—Flehr, Hohbach, Test, Albritton & Herbert

[57] ABSTRACT

Apparatus for introducing an ionized drug solution into the eye having a member formed of an insulating material adapted to be secured to the eye. The member has a nose which is adapted to come in contact with the eye and form a liquid-tight seal therewith. The member has a passageway therein with a cross sectional area of less than approximately 1 millimeter in diameter. An ionized drug solution fills the passageway. An electrical circuit is provided for causing current flow through the drug solution to cause a high voltage gradient and a high current density to be established in the eye in the vicinity of the portion of the eye in contact with the drug solution in the passageway to cause the drug solution to be carried from the passageway into the eye.

11 Claims, 3 Drawing Figures

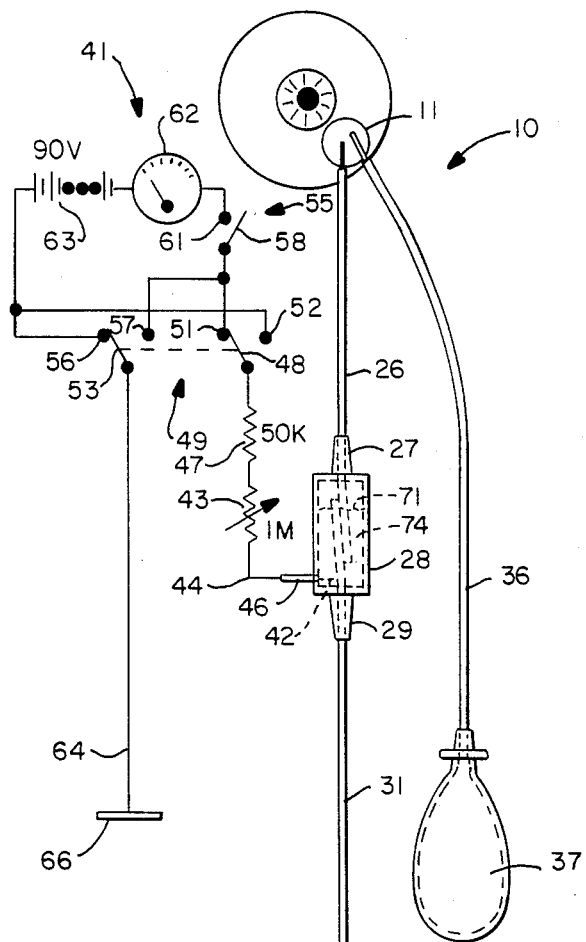
FIG.—1
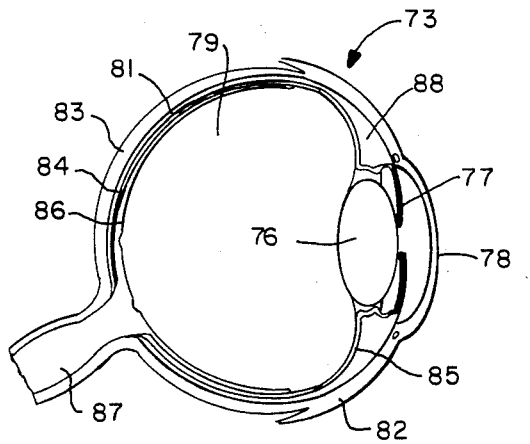
FIG.—2
FIG.—3

APPARATUS FOR INTRODUCING IONIZED DRUGS INTO THE POSTERIOR SEGMENT OF THE EYE AND METHOD

This is a continuation of application Ser. No. 381,151 filed May 24, 1982 now abandoned.

This invention relates to an apparatus and method for introducing ionized drugs into the eye and more particularly into the posterior segment of the eye.

The introduction of drugs into the eye by iontophoresis has been attempted for many years and is discussed in the literature. In the literature of particular interest is Sir Stewart Duke-Elder's article in *System of Ophthalmology*, published by S. V. Mosby, St. Louis, Mo. Volume VII, pages 507–514, (1962), an article by Ludwig von Sallman in *Transactions of the American Ophthalmological Society*, Volume 45, Page 570 (1947) entitled "Controversial Points In Ocular Penicillin Therapy", and an article entitled "Ein neues Instrument zur Behandlung des septischen Hornhautgeschwurs mittels Iontophorese" by Dr. Lubowski, published in *Klinische Medizin*, Volume 7, Page 1658 (1911). From these articles it can be seen that ocular iontophoresis has not been widely accepted and has at best met with only limited success in certain applications. In the past there has been difficulty in the treatment of diseases in the posterior of the eye, particularly in the case of infections in that part of the eye because of the difficulty of introducing drugs across the barriers set up by the eye to protect the retina as, for example, the cellular barriers posed by the conjunctival epithelium and the pigment epithelium. There is therefore, a particular need to introduce drugs into the posterior portion of the eye. Drugs have been introduced into the posterior portion of the eye by injection of drugs through a needle directly into the vitreous body of the eye. The use of a needle for such a purpose has disadvantages particularly in that it is possible to damage the eye. There is therefore a need for a new and improved method and apparatus for introducing drugs into the eye.

In general, it is an object of the invention to provide an apparatus and a method for introducing ionized drugs into the eye.

Another object of the invention is to provide an apparatus and method of the above character which is particularly adapted for introducing ionized drugs into the posterior segment of the eye.

Another object of the invention is to provide an apparatus and method of the above character which can be used with ionized drugs having either negative ions or positive ions.

Another object of the invention is to provide an apparatus of the above character in which the portion of the apparatus in engagement with the eye has a low profile which helps to prevent dislodgement by the eyelids when the eyelids move relative to the eye or when the eye rotates in its orbit.

Another object of the invention is to provide an apparatus of the above character which is relatively simple and which can be readily used.

Additional objects and features of the present invention will appear from the following description in which the prefered embodiment is set forth in conjunction with the accompanying drawing.

FIG. 1 is a front elevational view of the apparatus for introducing ionized drugs into the posterior segment of the eye with certain portions of the same being illustrated schematically.

FIG. 2 is an enlarged cross sectional view showing the apparatus and manner in which the apparatus is secured to the eye.

FIG. 3 is a cross sectional view of a human eye.

The apparatus 10 for introducing ionized drugs into the posterior segment of the eye consists of a suction cup or dish-shaped member 11 which is formed of a suitable insulating material which is preferably transparent. One material which has been found to be particularly satisfactory is one which has been formed from "Lucite". For reasons hereinafter explained, the suction cup although it can be relatively thin walled, should also be relatively rigid. As shown in FIG. 2, the suction cup is substantially dish-shaped and is provided with an outer depending annular portion 12 which is adapted to engage the eye as shown particularly in FIG. 2. The suction cup can be of a size ranging from 5 to 15 millimeters in diameter but preferably ranging from 8 to 9 millimeters in diameter. The suction cup 11 is provided with a centrally disposed nose or nipple 13 which has its outer extremity lying generally in the plane in which the annular portion 12 lies. The outer extremity of the nose or nipple 13 has a relatively small cross sectional area in the vicinity of 1.0 to 2.0 millimeters in diameter in comparison to the total area covered by the suction cup 11.

The suction cup 11 is provided with a flow passage 16 which is centrally disposed in the nozzle or nipple 13 and opens through the same as shown particularly in FIG. 2. The flow passage 16 is of small cross sectional area and has a diameter less than one millimeter and preferably a diameter in the range of 0.25 to 0.5 millimeters. A tubular member 17 is formed integral with the suction cup 11 and extends into the suction cup in a direction which is generally parallel to the plane of the annular portion 12 and is provided with a flow passage 18 which is in communication with the flow passage 16. The suction cup 11 is also provided with another tubular member 19 which is formed integral with the suction cup. It is provided with a flow passage 21 which opens into the interior of the suction cup 11 and is provided as hereinafter described for withdrawing air from the suction cup to establish a pressure below atmospheric in the suction cup. The tubular members 17 and 19 are also formed of a insulating material and are preferably transparent as is the suction cup 11. Typically, the suction cup 11 and the nose or nipple 13 and the tubular members 17 and 19 would be formed of the same material. As shown, the tubular members 17 and 19 extend outwardly in a plane parallel to the plane in which the annular portion 12 lies. In addition the tubular members 17 and 19 extend in generally the same direction, as as for example, when the suction cup 11 is secured to the eye they extend outwardly from the eye as shown in FIG. 2.

A small soft flexible tube 26 preferably formed of a transparent plastic material has one end connected to the tubular member 17 and has the other end connected into an outlet 27 of a cylindrical container 28. The container 28 is provided with an inlet which is connected to one end of a flexible tube 31. The other end of the flexible tube 31 is connected to an outlet of a conventional syringe 33 typically formed of a plastic material. The syringe 33 is provided with a hand operated plunger 34.

The container 28 is formed of a suitable insulating material such as a transparent plastic. As can be seen, the tubes 26 and 31 extend inwardly into the container in such a manner so that they extend beyond each other to a substantial extent. Thus as shown, the tube 31 extends upwardly for over three quarters of the distance into the container 28 whereas the tube 26 extends downwardly into the container for over one-half of the distance in the container.

The container 28 can have any desired configuration as for example, a cylindrical configuration as shown in FIG. 1. It is formed of a suitable insulating material such as a transparent plastic. It is preferably of a size which can hold a predetermined amount of a fluid as, for example 1 cc.

A soft flexible tube 36 has one end connected to the tubular member 19. The other end of the flexible tube 36 is connected to a bulb 37 of a conventional type. Both the flexible tube 36 and the bulb 37 are preferably formed of a suitable insulating material. For example, the flexible tube 36 can be formed of a transparent plastic whereas the bulb can be formed of a natural rubber.

Electrical circuit means is provided for supplying a current to the ionized liquid such as an ionized drug solution which may be disposed within the container 28 to create a high voltage gradient and a high current density in the vicinity of the portion of the eyeball in contact with the passageway 16. This electrical circuit means 41 consists of an electrode 42 formed of a suitable conducting material such as copper which penetrates the side wall forming the container 28 and extends into the container 28 near the lower extremity of the same as shown particularly in FIG. 1. The electrode 42 is connected to one terminal of a potentiometer 43 of a suitable resistance value such as one megohm by a conductor 44 covered by insulation 46. The other terminal of the potentiometer 43 is connected to one end of a resistor 47 of a suitable value so as to provide a minimum resistance in the circuit such as 50,000 ohms to prevent accidental damage to the eye. The other end of the resistor 47 is connected to a movable contact 48 of a double pole, double throw switch 49. The movable contact 48 is adapted to engage one of two stationary contacts 51 and 52. The switch 49 is provided with another movable contact 53 which is adapted to engage alternatively stationary contacts 56 and 57. The contact 57 is connected to a movable contact 58 of an off-on switch 55. The movable contact 58 is adapted to engage a stationary contact 61. The contact 61 is connected to one side of a meter 62 and the other side of the meter 62 is connected to the negative side of a battery 63. The battery 63 can be of any suitable voltage providing a desired current flow, as for example, a battery providing 90 volts DC. The positive terminal of the battery 63 is connected to the stationary contacts 52 and 56. The movable contact 53 is connected by a conductor 64 to an electrode 66. This electrode 66 may be characterized as an indifferent electrode. The electrode 66 is formed of a suitable conducting material such as copper.

Operation and use of the apparatus shown in FIGS. 1 and 2 may now be briefly described in conjunction with performing the method of the present invention. Let it be assumed that it is desired to introduce a desired drug into the eye and particularly into the posterior portion or segment of the eye. As it is well known to those skilled in the art, many drugs are ionized or electrically charged; that is, they are in the form of cations or anions. Such drugs include aminoglycosides, penicillins, some steroids and fluorescein.

Now let it be assumed that it is desired to administer one of these drugs by iontophoresis to the posterior portion of the eye as, for example, gentamicin or fluorescein. The desired ionized drug solution is introduced into the syringe 33 in a conventional manner by withdrawing the plunger 34 and drawing the drug into the interior of the syringe. The syringe is then connected to the flexible tube 31 and a desired quantity of the drug is introduced into the flexible tube 31 and into the container 28. During the time that the plunger 34 of the syringe 33 is being operated to accomplish this, the container 28 is inverted from the position shown in FIG. 1 so that the drug gradually begins to fill the container 28 by filling from the top which is now the bottom. This causes any air in the chamber 28 to move upwardly in the inverted chamber 28 and to be forced out through the dish-shaped member or suction cup 11. The syringe is used to continually introduce the liquid drug into the container 28 until the liquid reaches the upper extremity of the tube 26 in the inverted container 28 at which time the liquid will enter the tube 26 and will be forced out of the passage 16 to clear all the air out of the flexible tubular members 31 and 26. During this time, a small air pocket will remain in the upper portion of the inverted container 28. After this filling operation has been completed, the inverted chamber is returned to its normal upright position, shown in FIG. 1. As soon as this occurs, the air pocket which is within the chamber 28 will move to the upper extremity of the chamber 28 so that the liquid level 71 is substantially above the lower extremity of the flexible tube 26.

As soon as it has been decided where it is desired to place the suction cup 11, the suction cup 11 is held by one hand and the bulb 37 is compressed with the other hand and while the bulb 37 is held compressed, the suction cup 11 with its nose 13 are pressed into contact with the exterior surface of the anesthesized eye in the position hereinbefore indicated to form fluid-tight seals before the bulb 37 is released. The suction bulb 37 is then released by the hand which causes suction by withdrawal of air through the passage 21 of the tubular member 19 from the space 72 which is in communication with the flow passage 21. This reduction of pressure in the space 72 causes the outside atmospheric pressure to apply pressure to the exterior of the suction cup 11 to compress it into engagement with the eyeball 73 as shown in FIG. 2 to form an air-tight seal between the annular portion 12 and the eyeball 73. At the same time that this is occurring, the reduction in pressure in the space 72 causes the portion of the eyeball 73 disposed opposite the space 72 to bulge outwardly into the space and to maintain a sealing engagement with the nose or nozzle 13. The space 72 should be sufficiently deep so that when the eyeball 73 bulges outwardly the eyeball 73 does not block the suction passage 21 in the tubular member 19.

It should be noted that the suction cup 11 and the soft flexible tubes 26 and 36 have a low profile so that the suction cup 11 will not be dislodged when the eyelids move relative to the eyeball 73 or when the eyeball 73 rotates in its orbit. The soft flexible tubes 26 and 36 facilitate eyeball rotation.

In placing the apparatus in a condition so that it is ready for use, the electrode 66 is secured to the body of the patient in some appropriate place as, for example, the neck of the patient by means well known to those skilled in the art so as to make a low impedance electrical contact to the skin. The electrode 66 is connected to the body and the suction cup 11 is secured to the eye with the switch 59 in the open or off position. The potentiometer 43 is in the maximum resistance position. The switch 58 is then closed to cause current to flow in one direction or the other depending on the position of the switch 49. Assuming that a negatively ionized drug is to be used the switch 49 is moved to the position shown in FIG. 1 so that current flows from negative to positive the current will flow through the 50k resistance 47 and then through the potentiometer 43 to the electrode 42 and then into the ionized liquid 74 within the container 78. The current will flow through the liquid in the tube 26 and the liquid which is in contact with the eyeball 73 through the passageway 16 through the eyeball and through the human body to the electrode 66 back through the switch 49 to the positive side of the battery 63. The amount of current flow is observed on the meter 62. Current flow is then adjusted to the desired value by adjustment of the potentiometer 43 by decreasing the resistance to the appropriate value. Initially, typically the current flow could be as low as 0.1 milliampere and then is gradually increased to the desired value as, for example, to 1 milliampere for a flow passage 16 of a diameter of 0.25 to 0.5 millimeters. For a flow passage of a diamter of 0.25 millimeters, this is equivalent to a range of current density of 200 milliamperes to 2000 milliamperes per cm$^2$. For a flow passage of a diameter of 0.5 millimeters this is equivalent to a range of current density of 50 to 500 milliamperes per cm$^2$. When positively ionized drugs are to be utilized the switch 49 is moved to its other position in the direction, the direction of the current flow is reversed.

The current flow at its set value remains relatively constant because the value of the resistance of potentiometer 43 and resistance 47 is large in comparison to the resistance of eyeball and the ionized drug solution in the electrical circuit. The tube 26 is preferably kept relatively short and with a relatively large bore to provide a low electrical resistance through the ionized drug solution contained therein.

Because of the small cross-sectional area of the passageway 16, a high current density is established in the eyeball 73 in the vicinity of the exit from the passageway 16 in contact with the eyeball 73 to cause the drug in the ionized drug solution to move from the passageway 16 into the eyeball 73. It has been found that by causing a current flow of at least 50 milliamperes per square centimeter establishing a high current density in the immediate vicinity of the portion of the eyeball in contact with the drug solution in passageway 16, the ionized drug is caused to move quickly across the various barriers in the eye into the interior of the eyeball 73. As is well know to those skilled in opthalmology, the eyeball 73 as shown in FIG. 3 includes a lens 76 exposed to light through an iris 77 lying behind the cornea 78. The lens 76 is in contact with a vitreous body 79 which is in contact with the retina 81. The eyeball 73 includes various barrier layers between the ionized drug in contact with the eyeball 73 and the vitreous body 79. The barrier layers include the conjunctival epithelium 82, the sclera 83, the choroid 84, the pigment epithelium 85 and the retina 86. The retina 86 is connected to the optic nerve 87. The eyeball also includes a ciliary body 88 which is disposed between the forward annular margin of the retina 86 and the outer annular margin of the cornea 78.

It has been possible to visually observe the functioning of the apparatus in the introduction of a drug by iontophoresis into the posterior portion of the eye. This was accomplished utilizing fluorescein as representing the ionized drug solution. To accomplish this visual observation, the refractive power of the cornea of the eye was neutralized by pressing a glass plate against the surface of an anesthesized eye and the interior of the eye was illuminated and observed through the pupil. After switching on the current as hereinbefore described within approximately one minute fluorescein was observed inside the eye entering the eyeball at the point corresponding to where the electrode in the form of the fluid in the passageway 16 contacts the outside of the eyeball. This took the form of a bright green spot when first observed which after a period of a minute was seen to spread through the vitreous body of the eye to become substantially larger as, for example, several millimeters in diameter. Within a period of a few hours, it was found that the fluorescein occupied the entire vitreous body of the eye. By observing the action of the introduction of fluorescein with the present apparatus and having it diffuse throughout the entire interior of the eye, it is believed that an ionized drug introduced by the same apparatus would be diffused through the entire vitreous body of the eye.

A typical treatment can be accomplished within a period of a few minutes after which the apparatus can be removed by reducing the current flow by adjustment of the potentiometer 43 and then compressing the suction bulb 37 to cause the dish-shaped member to be released from the eyeball 73. Thereafter, after the drug has passed into the eyeball, it can be permitted to diffuse throughout the entire volume of the vitreous body to come in contact with the retina and the posterior portion or segment of the eyeball.

In the event there are any gases generated at the electrode 42 by introducing current into the liquid 74 in the container 28, such gases will rise to the upper portion of the container substantially above the lower extremity of the flexible tube 26 so that current flow will not be interrupted. Thus it can be seen that the container 28 serves a dual purpose. It serves to collect any air which may be present in the chamber 28 in an upper portion of the chamber so that air will not pass into the tube 26 to interrupt current flow and similiarly any gases which are generated at the electrode 42 by current passing through the liquid 74 also will not pass into the tube 26 and interrupt current flow. The volume of such gases generated at the electrode 42 is relatively small in comparison to the normal volume of air in the container 28 and therefore such gases generated at the electrode 42 will not substantially increase the pressure or the volume of the gas in the container 28. For this reason gas will not be forced into the passageway 16 during operation of the apparatus 10. Also it should be pointed out that any products of electrolysis produced in the drug solution around the electrode 42 will not come into contact with the eye but will normally remain in the container 28. The length of the tube 26 is such that the drug passing into the eye will come from the drug solution in the passageway 16 and in the tube 26.

By utilizing the present apparatus with the method hereinbefore described, it is possible to introduce antibiotics either for the purpose of treating established infections in the posterior segment of the eye or prophylactically when operations on the eye are contemplated to prevent an infection occuring during the course or subsequent to the operation on the eye. The apparatus of the present invention also should be useful for the introduction of anti-cancerous drugs into the eye and also for the introduction of drugs for treating non-infective inflammatory conditions in the posterior segment of the eye. In addition, the apparatus may be utilized for the introduction of fluorescein or other drugs for diagnostic purposes.

What is claimed is:

1. In an apparatus for introducing an ionized drug into the eye, a cup-shaped member formed of an insulating material and having an outwardly extending annular lip adapted to be placed in contact with the exterior scleral surface of the eye, said member having a nipple formed integral therewith disposed within the confines of the annular lip and having its outer extremity lying generally in the same plane as the plane of the annular lip, said annular lip and said nipple being adapted to come in contact with the eye and to form a liquid-tight seal therewith, said member having a passageway therein extending through the nipple with a cross-sectional area of less than approximately one millimeter in diameter, an ionized drug solution filling said passageway and electrical power supply means remote from the member and coupled to said passageway for causing a current flow of at least 50 milliamperes per square centimeter through the drug solution to establish a high current density in the eye in the vicinity of the portion of the eye in contact with the ionized drug solution in said passageway whereby the drug is carried from the passageway into the eye.

2. In an apparatus for introducing an ionized drug into the eye, a cup-shaped member formed of an insulating material and having an outwardly extending annular lip adapted to be placed in contact with the exterior scleral surface of the eye, said member having a nipple formed integral therewith disposed within the confines of the annular lip and having its outer extremity lying generally in the same plane as the plane of the annular lip, said annular lip and said nipple being adapted to come in contact with the eye and to form a liquid-tight seal therewith, said member having a passageway therein extending through the nipple with a cross-sectional area of less than approximately one millimeter in diameter, an ionized drug solution filling said passageway, electrical power supply means remote from the member and coupled to said passageway for causing current flow through the drug and a high current density to be established in the eye in the vicinity of the portion of the eye in contact with the ionized drug solution in said passageway to cause the ionized drug to be carried from the passageway into the eye, a liquid tight container, means for forming a flow passage from said liquid tight container to said passageway in said member, said container and said means forming a flow passage having said ionized drug solution therein and means within said container for accommodating gas in said chamber so as to prevent interrupting the flow of current through the ionized drug solution, said means for causing current flow including an electrode disposed in the ionized drug solution in said container.

3. Apparatus as in claim 2 wherein said means for accommodating gasses in said container without interrupting the current flow through the drug in the container includes first and second tubular members which extend beyond each other in the container.

4. In an apparatus for introducing an ionized drug into the eye, a cup-shaped member formed of an insulating material and having an outwardly extending annular lip adapted to be placed in contact with the exterior scleral surface of the eye, said member having a nipple formed integral therewith disposed within the confines of the annular lip and having its outer extremity lying generally in the same plane as the plane of the annular lip, said annular lip and said nipple being adapted to come in contact with the eye and to form a liquid-tight seal therewith, said member having a passageway therein extending through the nipple with a cross-sectional area of less than approximately one millimeter in diameter, an ionized drug solution filling said passageway and electrical power supply means remote from the member and coupled to said passageway for causing current flow through the drug and a high current density to be established in the eye in the vicinity of the portion of the eye in contact with the ionized drug solution in said passageway to cause the ionized drug to be carried from the passageway into the eye, said member being in the form of a suction cup and means secured to said suction cup for withdrawing air from said suction cup whereby said member may be secured to said eye by the use of suction.

5. In an apparatus for introducing an ionized drug into the eye, a cup-shaped member formed of an insulating material and having an outwardly extending annular lip adapted to be placed in contact with the exterior scleral surface of the eye, said member having a nipple formed integral therewith disposed within the confines of the annular lip and having its outer extremity lying generally in the same plane as the plane of the annular lip, said annular lip and said nipple being adapted to come in contact with the eye and to form a liquid-tight seal therewith, said member having a passageway therein extending through the nipple with a cross-sectional area of less than approximately one millimeter in diameter, an ionized drug solution filling said passageway and electrical power supply means remote from the member and coupled to said passageway for causing current flow through the drug and a high current density to be established in the eye in the vicinity of the portion of the eye in contact with the ionized drug solution in said passageway to cause the ionized drug to be carried from the passageway into the eye, said means for supplying a source of current to said drug including reversing means for supplying either a positive or negative voltage to said electrode.

6. In an apparatus for introducing an ionized drug into the eye, a cup-shaped member formed of an insulating material and having an outwardly extending annular lip adapted to be placed in contact with the exterior scleral surface of the eye, said member having a nipple formed integral therewith disposed within the confines of the annular lip and having its outer extremity lying generally in the same plane as the plane of the annular lip, said annular lip and said nipple being adapted to come in contact with the eye and to form a liquid-tight seal therewith said member having a passageway therein extending through the nipple with a cross-sectional area of less than approximately one millimeter in diameter, an ionized drug solution filling said passageway and electrical power supply means remote from the member and coupled to said passageway for causing current flow through the drug and a high current density to be established in the eye in the vicinity of the portion of the eye in contact with the ionized drug solution in said passageway to cause the ionized drug to be carried from the passageway into the eye, said passageway having a cross sectional area of 0.25 to 0.50 millimeters in diameter.

7. In an apparatus for introducing an ionized drug into the eye, a cup-shaped member formed of an insulating material and having an outwardly extending annular lip adapted to be placed in contact with the exterior scleral surface of the eye, said member having a nipple formed integral therewith disposed within the confines of the annular lip and having its outer extremity lying generally in the same plane as the plane of the annular lip, said annular lip and said nipple being adapted to come in contact with the eye and to form a liquid-tight seal therewith, said member having a passageway therein extending through the nipple with a cross-sectional area of less than approximately one millimeter in diameter, an ionized drug solution filling said passageway and electrical power supply means remote from the member and coupled to said passageway for causing current flow through the drug and a high current density to be established in the eye in the vicinity of the portion of the eye in contact with the ionized drug solution in said passageway to cause the ionized drug to be carried from the passageway into the eye, said member having a profile configured to minimize the possibility that movement of the eyelids will cause dislodgement of said member.

8. Apparatus as in claim 7 wherein small flexible tubular members are connected to said member.

9. In a method for introducing an ionized drug into the eye, placing an ionized drug solution in contact with an exterior scleral surface of the eye in a small area of the eye of less than approximately one millimeter in diameter, causing a current flow of at least 50 milliamperes per square centimeter through said ionized drug solution in said small area to establish a high current density in the eye in the vicinity of the portion of the eye in contact with the ionized drug solution whereby the drug is caused to pass into the eye.

10. A method as in claim 9 wherein the small area has a size ranging from 0.25 to 0.5 millimeters in diameter.

11. A method as in claim 9 together with the step of trapping gases generated during current flow through said ionized drug solution so that the gases will not interrupt the flow of current through the ionized drug solution.

* * * * *